(12) United States Patent
Conour

(10) Patent No.: US 9,066,949 B2
(45) Date of Patent: Jun. 30, 2015

(54) COMPOSITIONS AND METHODS FOR THE TREATMENT OF CATATONIA

(76) Inventor: James Conour, Portland, OR (US)

(*) Notice: Subject to any disclaimer, the term of this patent is extended or adjusted under 35 U.S.C. 154(b) by 0 days.

(21) Appl. No.: 14/005,348

(22) PCT Filed: Mar. 20, 2012

(86) PCT No.: PCT/US2012/029811
§ 371 (c)(1),
(2), (4) Date: Sep. 16, 2013

(87) PCT Pub. No.: WO2012/129232
PCT Pub. Date: Sep. 27, 2012

(65) Prior Publication Data
US 2014/0005173 A1    Jan. 2, 2014

Related U.S. Application Data

(60) Provisional application No. 61/454,622, filed on Mar. 21, 2011.

(51) Int. Cl.
| | |
|---|---|
| *A61K 31/53* | (2006.01) |
| *A61K 31/55* | (2006.01) |
| *A61K 31/519* | (2006.01) |
| *A61K 31/4406* | (2006.01) |
| *A61K 31/4515* | (2006.01) |
| *A61K 31/496* | (2006.01) |
| *A61K 31/517* | (2006.01) |
| *A61K 31/5415* | (2006.01) |
| *A61K 31/5513* | (2006.01) |
| *A61K 31/554* | (2006.01) |
| *A61K 45/06* | (2006.01) |
| *A61K 31/405* | (2006.01) |
| *A61K 31/5517* | (2006.01) |

(52) U.S. Cl.
CPC ........... *A61K 31/519* (2013.01); *A61K 31/4406* (2013.01); *A61K 31/4515* (2013.01); *A61K 31/496* (2013.01); *A61K 31/517* (2013.01); *A61K 31/53* (2013.01); *A61K 31/5415* (2013.01); *A61K 31/5513* (2013.01); *A61K 31/554* (2013.01); *A61K 45/06* (2013.01); *A61K 2300/00* (2013.01); *A61K 31/405* (2013.01); *A61K 31/5517* (2013.01)

(58) Field of Classification Search
CPC .............. A61K 31/55; A61K 31/5513; A61K 31/5415; A61K 31/53
USPC .......................................... 514/241, 218, 221
See application file for complete search history.

(56) References Cited

U.S. PATENT DOCUMENTS 4,588,721 A * 5/1986 Mahan .................. 514/220

FOREIGN PATENT DOCUMENTS

| WO | 2006067494 A1 | 6/2006 |
|---|---|---|
| WO | 2008038003 A2 | 4/2008 |
| WO | 2008125843 A1 | 10/2008 |

OTHER PUBLICATIONS

Hunt et al., "Modulation of high-frequency oscillations associated with NMDA receptor hypofunction in the rodent nucleus accumbens by lamotrigine", Progress in Neuro-Psychopharmacology & Biological Psychiarty, vol. 32, No. 5, pp. 1312-1319 (2008).*
Stahl, et al., "A Critical Review of Atypical Antipsychotic Utilization: Comparing Monotherapy with Polypharmacy and Augmentation," Current Medicinal Chemistry, 2004, vol. 11, No. 3, pp. 313-327.
Tiihonen, et al., "The Efficacy of Lamotrigine in Clozapine-Resistant Schizophrenia: A Systematic Review and Meta-Analysis," Schizophrenia Research, 2009, vol. 109, pp. 10-14.
Zoccali, et al., "The Effect of Lamotriginc Augmentation of Clozapine in a Sample of Treatment-Resistant Schizophrenic Patients: A Double-Blind, Placebo-Controlled Study," Schizophrenia Research, 2007, vol. 93, pp. 109-116.
Goff, et al., "Lamotrigine as Add-On Therapy in Schizophrenia, Results of 2 Placebo-Controlled Trials," Journal of Clinical Psychopharmacology, Dec. 2007, vol. 27, No. 6, pp. 582-589.
Dursun, et al., "Augmenting Antipsychotic Treatment with Lamotrigine or Topiramate in Patients with Treatment-Resistant Schizophrenia: a Naturalistic Caseseries Outcome Study," Journal of Psychopharmacology, 2001, vol. 15, No. 4, pp. 297-301.
Glick, et al., "A Double-Blind Randomized Trial of Mood Stabilizer Augmentation Using Lamotrigine and Valproate for Patients with Schizophrenia Who Are Stabilized and Partially Responsive," Journal of Clinical Psychopharmacology, Jun. 2009, vol. 29, No. 3, pp. 267-271.
International Preliminary Report on Patentability dated Sep. 24, 2013, International App. No. PCT/US2012/029811, 6 pages.
International Search Report for International Application No. PCT/US2012/029811 dated Jun. 8, 2012.
"If one would have Catatonia while taking Lamotrigine, who are they, when it happens and how?", eHealthMe, Mar. 24, 2011, <http://www.ehealthme.com/ds/lamotrigine/catatonia>.
England et al., "Catatonia in Psychotic Patients: Clinical Features and Treatment Response", The Journal of Neuropsychiatry and Clinical Neurosciences, Spring 2011, vol. 23:, pp. 211-226.
Kremer et al., "Placebo-Controlled Trial of Lamotrigine Added to Conventional and Atypical Antipsychotics in Schizophrenia", Biol Psychiatry, 2004, vol. 56, pp. 441-446.

* cited by examiner

*Primary Examiner* — Kevin E Weddington
(74) *Attorney, Agent, or Firm* — Quarles & Brady LLP

(57) ABSTRACT

Compositions and methods for treating psychotic and neurological disorders in a subject are disclosed. The compositions and methods utilize a pharmaceutical compound that reverses or negates the effects of an NMDA receptor antagonist. The compositions and methods are effective in reducing at least catatonic features in the subject.

5 Claims, No Drawings

COMPOSITIONS AND METHODS FOR THE TREATMENT OF CATATONIA

CROSS-REFERENCE TO RELATED APPLICATIONS

This application represents the national stage entry of PCT International Application No. PCT/US2012/029811 filed on Mar. 20, 2012 and claims the benefit of U.S. Provisional Application Ser. No. 61/454,622 filed Mar. 21, 2011, both of which are incorporated herein by reference.

FIELD OF INVENTION

Treatment of psychotic and neurological disorders with catatonic features.

BACKGROUND

Schizophrenic disorders (inclusively, given the current nosological framework, this may be schizoaffective disorder, schizophreniform disorder, and the subtypes of schizophrenia), a type of psychotic disorder, are complicated psychiatric illnesses with protean behavioral manifestations. These disorders are characterized by the onset of hallucinations, delusional processing, behavioral changes, mood instability, cognitive impairments, and disorganized thinking. Affected individuals typically start showing clinical signs in adolescence and early adulthood. These signs and symptoms are typically experienced and/or demonstrated for life and usually have a profound impact on daily functioning.

Males have been shown statistically to have an earlier onset than females. Clinically, earlier onset tends to result in a more intractable, treatment resistant prognosis. It is also apparent that there is genetic loading for these disorders as it noted epidemiologically that there is familial clustering. While the exact genetic loci and mechanistic underpinnings are not fully understood at this time, it is known from twin studies that monozygotic twins have a concordance rate above 40% for the disorder. Moreover, while there are clearly non-genetic factors accounting for schizophrenic disorders as well, these factors are also not fully delineated at this time.

Current efforts to understand schizophrenia on a neurotransmitter/molecular level have focused on the observed alterations in glutamate and dopamine (glutamatergic and dopaminergic hypotheses). Imaging technologies such as functional magnetic resonance imaging (fMRI) have shown morphologic brain changes that demonstrate the significant and global loss of gray matter in neocortical regions. It is likely, based upon other studies that there are subcortical losses, as well. Current evidence may support the proposition that the severity of schizophrenic disorders increases with greater gray matter volumetric losses. Additionally, it is noted that cortical changes in schizophrenics include a reduced number and/or functionality of interneurons and thus a dysregulation of excitatory neurons. (Benes F M, Berretta S. GABAergic interneurons: implications for understanding schizophrenia and bipolar disorder. Neuropsychopharmacology 2001 July; 25(1):1-27; Lodge D J, Behrens M M, Grace A A. A loss of parvalbumin-containing interneurons is associated with diminished oscillatory activity in an animal model of schizophrenia. J Neurosci, 2009 Feb. 25; 29(8):2344-2354; Spencer K M, Nestor P G, Niznikiewicz M A, Salisbury D F, Shenton M E, McCarley R W. Abnormal neural synchrony in schizophrenia. J Neurosci., 2003 Aug. 13; 23(19):7407-11).

Epidemiological data indicate that schizophrenic disorders are endemic globally in all human populations and have a prevalence of approximately 1% worldwide. Furthermore, when combining the prevalence of other psychotic disorders such as bipolar disorder type 1, unipolar depression with psychosis, and delusional disorders with schizophrenic disorders, a total worldwide prevalence of approximately 3% is reached.

Schizophrenic patients present clinicians with a cloud of symptom clusters and idiosyncratic behaviors. Often, patients have co-morbid anxiety disorders such as OCD or affective disorders such as depression. It can be quite difficult to accurately collect the pertinent data that would aid in diagnosis or demonstrate improvement with a given treatment plan. Despite these diagnostic difficulties, it has become apparent that a significant proportion of these patients have previously unrecognized catatonic features intertwined with psychotic features. Indeed, it may be catatonic features that largely contribute to their so-called treatment resistance. These features are usually chronically present, though some individuals have a dynamic, episodic presentation. Indeed, some patients seem to manifest catatonic features only when fully decompensated due to poor medication adherence.

The treatment for psychotic disorders is primarily pharmacologically based. Medication treatment plans include antipsychotics mood stabilizers, antidepressants, and sedative/hypnotics. Of the aforementioned categories, antipsychotics and mood stabilizers are the primary pharmacological interventions. These classes of medications are often used in various combinations and titrated to various dosages based upon observed clinical effect. Schizophrenic disorders are often less responsive to treatment than other psychotic disorders such as Bipolar disorder type 1. While some individuals can show a good response in that they have remission of the symptoms of psychosis, a significant proportion of those receiving treatment are moderate, marginal, or non-responders. Indeed, the literature notes that from 20 to 60% of individuals with schizophrenic disorders are defined as treatment resistant.

Moreover, it is additionally noted that individuals suffering from other neurological disorders including, for example, Alzheimer's type dementia and severe forms of autism may have a poor response to conventional treatment due to the co-morbidity of catatonic features. Thus, as is believed for psychotic disorders, the reduction or elimination of the catatonic features may enable clinicians to improve treatment response in a number of other psychiatric/neurological disorders. Herein, a treatment for catatonic features in individuals suffering therefrom alone or in addition to other psychotic and/or neurological disorders is disclosed.

SUMMARY OF THE INVENTION

In a first aspect, a method of treating a psychotic or neurological disorder having catatonic features in a subject in need thereof, includes administering to the subject a therapeutically effective amount of a pharmaceutical compound that reverses or negates the effects of an NMDA receptor antagonist for a period of at least about 2 weeks to decrease the subject's BFCRS score by at least 4.

In another embodiment, the amount of the pharmaceutical compound is at least about 25 mg per day and the NMDA receptor antagonist is ketamine.

In a further embodiment, the pharmaceutical compound is selected from the group consisting of lamotrigine, quetiapine, chlorpromazine, cotinine, and combinations thereof.

In an additional embodiment, administration of at least about 50 mg per day of the pharmaceutical compound to a patient in need thereof for a period of about 4 weeks results in a decrease in the patient's BFCRS score of about 6.

In a further embodiment, the psychotic or neurological disorder comprises catatonia, schizophrenia, Alzheimer's, dementias, autism, and combinations thereof.

In another embodiment, the composition further includes a therapeutically effective amount of a benzodiazepine.

In a second aspect, a composition includes a therapeutically effective amount of an antipsychotic agent, a therapeutically effective amount of a pharmaceutical compound that reverses or negates the effects of an NMDA receptor antagonist and reduces catatonic features in a subject having a psychotic or neurological disorder, and an optional therapeutically effective amount of a benzodiazepine.

In another embodiment, the therapeutically effective amount of the antipsychotic is at least about 1 to about 1200 mg, the therapeutically effective amount of the pharmaceutical compound is at least about 25 to about 600 mg, and the optional therapeutically effective amount of the benzodiazepine is at least about 500 to about 10,000 µg.

In a further embodiment, the antipsychotic agent is selected from the group consisting of clozapine, olanzapine, risperidone, quetiapine, chlorpromazine, aripipazole, perphenazine, haloperidol, and combinations thereof.

In an additional embodiment, the NMDA receptor antagonist is ketamine.

In a further embodiment, the pharmaceutical compound is lamotrigine.

In another embodiment, the antipsychotic agent is selected from the group consisting of clozapine and olanzapine and the pharmaceutical compound is lamotrigine.

In a further embodiment, a pharmaceutical dosage form include a composition including a therapeutically effective amount of an antipsychotic agent, a therapeutically effective amount of a pharmaceutical compound that reverses or negates the effects of an NMDA receptor antagonist in a subject having a psychotic or neurological disorder comprising catatonic features, and an optional therapeutically effective amount of a benzodiazepine and one or more pharmaceutically suitable carriers, diluent, and/or excipients.

In another embodiment, the dosage form includes an oral, injection, infusion, inhalation, transdermal, or implant dosage form.

In an additional embodiment, the pharmaceutical dosage form comprises about 25 to about 600 mg of lamotrigine, about 500 to about 10,000 µg of a benzodiazepine, and either about 25 to about 1200 mg of clozapine or about 5 to about 60 mg of olanzapine.

In a further embodiment, the pharmaceutical dosage form comprises about 25 to about 100 mg of lamotrigine, about 500 to about 4000 µg of a benzodiazepine, and either about 25 to about 200 mg of clozapine or about 5 to about 30 mg of olanzapine.

In yet another embodiment, the pharmaceutical dosage form comprises about 25 mg of lamotrigine, about 500 µg of a benzodiazepine, and either about 25 mg of clozapine or about 5 mg of olanzapine.

In a third aspect, a method of treating a subject for catatonic schizophrenia, includes administering a treatment regimen to the subject including a therapeutically effective amount of an antipsychotic agent selected from the group consisting of clozapine and olanzapine, and a therapeutically effective amount of a pharmaceutical compound that reverses or negates the effects of an NMDA receptor antagonist in the subject. The treatment regimen includes administering at least about 200 mg per day of the pharmaceutical compound to the subject for a period of at least about 1 month to result in a decrease in the patient's BFCRS score of about 15.

In another embodiment, the treatment regimen is administered from a first kit that comprises the antipsychotic and the pharmaceutical compound in a combined formulation or from a second kit that comprises the antipsychotic and the pharmaceutical compound in separate pharmaceutical dosage forms, wherein the pharmaceutical dosage forms of the second kit may be administered to a patient at the same time or one at a time.

In a further embodiment, the subject exhibits a gain of function improvement.

DESCRIPTION

In patients suffering from psychotic disorders such as schizophrenia, there are several possible reasons for a poor response to prescribed treatments; however, one main reason is the limited clinical efficacy of various antipsychotics in many cases even when subjects have received multiple medications with adequate trials. Moreover, those with schizophrenic disorders who are poor responders tend to struggle with significant cognitive impairments that greatly impact day to day executive functioning, social interactions, and self-care. Taken with the other prominent signs and symptoms of this chronic condition, those affected will frequently require placement in long term institutions due to a lack of safety when living unsupported in the community.

Institutionalized subjects have typically been placed on a variety of treatment plans including various typical/atypical antipsychotics, mood stabilizers, antidepressants, and hypnotics. However, a large number of institutionalized subjects remain severely cognitively impaired due to various schizophrenic disorders. It has now been observed and demonstrated that these subjects have significant cognitive improvements, in fact, many have quite profound improvements, when treated with a core group of medications that have yielded greater clinical efficacy than conventional treatment plans.

For example, affected individuals who had previously been poor treatment responders have shown signs of improvement in their hallucinations and delusions. While such improvements are significant, potentially the most beneficial component of treatment response has been an increase in the preponderance of spontaneous, organized thoughts/behaviors in many observable domains. Acutely unsafe behaviors such as agitation or aggression become reliably quiescent as well. These psychiatric improvements can allow some individuals, who have spent many years being chronically institutionalized, to step down into less restrictive community environments in a safe and sustainable manner. For others it ensures that they are able to avoid being hospitalized, retain or transition to independent housing, or avoid becoming involved in the criminal justice system. Thus, the care burden as well as the cumbersome cost (which can be approximately 10,000 to 20,000 dollars per month for one subject in a secure setting for example) can be greatly reduced. The following non-limiting medications have been observed in achieving this meaningful clinical response and useful in the present disclosure.

The antipsychotic clozapine (sold as Clozaril® by Novartis Pharmaceuticals Corporation, East Hanover, N.J.) is a dibenzodiazepine with the chemical name 8-chloro-11-(4-methylpiperazin-1-yl)-5H-dibenzo[b,e][1,4]diazepine. Clozapine is well known in the literature for having greater efficacy in treating schizophrenic disorders than other antipsychotics. Additionally, it has been noted that on average subjects will need blood levels of clozapine to be approximately 400 ng/dl or higher to achieve greater clinical efficacy. Another antipsychotic is olanzapine (sold as Zyprexa® by Eli Lilly and Co., Indianapolis, Ind.). Olanzapine is a thienobenzodiazepine with the chemical name 2-methyl-4-(4-methyl-1-piperazinyl)-10H-thieno[2,3-b][1,5]benzodiazepine, that also shows some evidence of greater efficacy in the literature. Olanzapine has been reported to typically require dosages of greater than 30 mg per day to achieve differential results. Additionally, contemplated antipsychotics include quetiapine (sold as Seroquel® by AstraZeneca) and chlorpromazine (sold as Thorazine in the United States). Additionally, it has been observed that an augmentation strategy of combining an antipsychotic with lamotrigine, an anticonvulsant sold as Lamictal® (GlaxoSmithKline, Brentford, Middlesex, UK), has resulted in additional benefit when added to antipsychotic treatment regimens.

Treatment plans involving clozapine and olanzapine have been superior to other antipsychotics plans and their apparent superiority can be further improved when either is paired with lamotrigine. However, any antipsychotic may be used. Subjects tolerate the addition of lamotrigine quite well, and they often show maximal responses when it is titrated to a full dosage of 200 mg twice per day, but have exhibited meaningful reduction in catatonic features with as little as 25 mg per day.

In identifying reasons for why subjects may respond to these medications it has been observed clinically that they have had heretofore undiagnosed catatonia as a part of their complex and varied presentations. This may indicate that a large percentage of schizophrenics defined as treatment resistant in fact have a high proportion of catatonic features in addition to their other psychotic symptoms. It appears that it is the combination of these two dysfunctional symptom clusters that may create this diagnostically challenging and difficult to treat population.

Catatonia is a neurological syndrome that can occur comorbidly in a variety of psychiatric disorders. It presents with a constellation of observable behaviors in seemingly, odd grimaces, perseverative speech/behaviors, contrary/negativistic behaviors, mimicking behaviors, over-obedience, and several physical neurological findings. Additionally, it should be noted that some subjects can have particular components of their catatonia that make them manifestly unsafe. For example some subjects can be combative or violent while others withdraw and become alarmingly malnourished. Many of these features are interpreted as personality traits and go unnoticed in a variety of clinical contexts. Catatonia is identifiable in mood disorders such as severe unipolar depression and bipolar mania. Catatonia can also be observed with many other medical and psychiatric illnesses. Neurological disorders such as autistic spectrum disorders and dementia such as Alzheimer's disease are often associated with it. There are variants of catatonia, with malignant catatonia being a life threatening emergency. Catatonia, as a comorbid neurological syndrome, has most consistently been known to respond to electroconvulsive therapy and benzodiazepines. Benzodiazepine pharmacotherapy is the most common treatment modality and of the benzodiazepines (for example, diazepam, clonazepam, and lorazepam) lorazepam is the most prevalently utilized.

Mechanistically, catatonia is not fully understood, though there is evidence from fMRI studies that catatonic subjects have altered activity in supplemental motor areas, orbitofrontal cortices, and parietal cortices. Additionally, other studies have suggested low gama-aminobutyricacid (GABA)-A receptor binding, dopaminergic hypoactivity, and glutamatergic hyperactivity. Of particular significance, it has been shown that catatonia and psychotic symptoms consistent with schizophrenic disorders can be induced with ketamine, an NMDA receptor antagonist (other NMDA receptor agents that may mimic the effects of ketamine have not been found to be as safe neurologically).

The aforementioned medications clozapine, olanzapine, and lamotrigine all have been found to reverse the clinical effects of ketamine, which suggests that these medications are all able to address glutamatergic hyperactivity and likely have direct or indirect effects on NMDA receptors and, thus, catatonia. Most other antipsychotics, while they do address the dopaminergically-mediated components of psychosis, do not impact the effects of ketamine (e.g., risperidone, haloperidol). Furthermore, this suggests that other antipsychotics or psychopharmacological agents that reverse the clinical effects of NMDA receptor antagonists such as ketamine may also in fact have an anti-catatonia benefit as well, and therefore, may be useful in treating psychotic disorders that include catatonic features. Some of these agents may include agents that act at nicotinic receptors, such as nicotine and nicotine derivatives, for example, cotinine.

The present disclosure contemplates pharmaceutical formulations, dosage forms, kits, and methods wherein a compound, such as a pharmaceutical compound, that reverses or negates the effects of an NMDA receptor antagonist or mimic thereof is included to reduce catatonic features in a subject in need thereof. For example, contemplated pharmaceutical formulations, dosage forms, kits, and methods include an antipsychotic drug combined with a pharmaceutical compound that reverses or negates the effects of an NMDA receptor antagonist or mimic thereof. For example, a contemplated dosage form or method may employ an antipsychotic and lamotrigine. In another embodiment, a contemplated dosage form may employ clozapine and lamotrigine. In a further embodiment, a contemplated dosage form may employ olanzapine and lamotrigine.

The contemplated pharmaceutical formulations, dosage forms, kits, and methods may further include a plurality of antipsychotic drugs or pharmaceutically acceptable salts or derivatives thereof and one or more compounds that reverse or negate the effects of an NMDA receptor antagonist or a pharmaceutically acceptable salt or derivative thereof together with one or more pharmaceutically acceptable carriers therefor, and optionally, other therapeutic and/or prophylactic ingredients. The carrier(s) should be acceptable in the sense of being compatible with the other ingredients of the formulation and being physiologically acceptable to the recipient thereof.

For example, compositions herein may be formulated for oral, rectal, nasal, topical (including buccal and sublingual), transdermal, vaginal, injection/injectable, and/or parental (including subcutaneous, intramuscular, intravenous, and intradermal) administration. Other suitable administration routes are incorporated herein. The compositions may be presented conveniently in unit dosage forms and may be prepared by any methods known in the pharmaceutical arts. Examples of suitable drug formulations and/or forms are discussed in, for example, Hoover, John E. Remington's Pharmaceutical Sciences, Mack Publishing Co., Eston, Pa.; 18.sup.th edition (1995); and Liberman, H. A. and Lachman, L. Eds., Pharmaceutical Dosage Forms, Marcel Decker, New York, N.Y., 1980. Illustrative methods include the step of bringing one or more active ingredients into association with a carrier that constitutes one or more accessory ingredients. In general, the compositions may be prepared by bringing into association uniformly and intimately one or more active ingredients with liquid carriers or finely divided solid carriers or both, and then, if necessary, shaping the product.

Pharmaceutical formulations may include those suitable for oral, intramuscular, rectal, nasal, topical (including buccal and sub-lingual), vaginal or parenteral (including intramuscular, subcutaneous and intravenous) administration or in a form suitable for administration by inhalation or insufflation. One or more of the compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

A salt may be a pharmaceutically suitable (i.e., pharmaceutically acceptable) salt including, but not limited to, acid addition salts formed by mixing a solution of the instant compound with a solution of a pharmaceutically acceptable acid. A pharmaceutically acceptable acid may be, for example, hydrochloric acid, methanesulphonic acid, fumaric acid, maleic acid, succinic acid, acetic acid, benzoic acid, oxalic acid, citric acid, tartaric acid, carbonic acid or phosphoric acid.

Suitable pharmaceutically-acceptable salts may further include, but are not limited to salts of pharmaceutically-acceptable inorganic acids, including, for example, sulfuric, phosphoric, nitric, carbonic, boric, sulfamic, and hydrobromic acids, or salts of pharmaceutically-acceptable organic acids such propionic, butyric, maleic, hydroxymaleic, lactic, mucic, gluconic, benzoic, succinic, phenylacetic, toluenesulfonic, benzenesulfonic, salicyclic sulfanilic, aspartic, glutamic, edetic, stearic, palmitic, oleic, lauric, pantothenic, tannic, ascorbic, and valeric acids.

Various pharmaceutically acceptable salts include, for example, the list of FDA-approved commercially marketed salts including acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, mitrate, pamoate, pantothenate, phosphate, diphosphate, polygalacturonate, salicylate, stearate, subacetate, succinate, sulfate, tannate, tartrate, teoclate, and triethiodide.

A hydrate may be a pharmaceutically suitable (i.e., pharmaceutically acceptable) hydrate that is a compound formed by the addition of water or its elements to a host molecule (for example, the free form version of the compound) including, but not limited to, monohydrates, dihydrates, etc.

A solvate may be a pharmaceutically suitable (i.e., pharmaceutically acceptable) solvate, whereby solvation is an interaction of a solute with a solvent which leads to stabilization of the solute species in a solution, and whereby the solvated state is an ion in a solution complexed by solvent molecules. Solvates and hydrates may also be referred to as "analogues."

A prodrug may be a compound that is pharmacologically inert but are converted by enzyme or chemical action to an active form of the drug (i.e., an active pharmaceutical ingredient) at or near the predetermined target site. In other words, prodrugs are inactive compounds that yield an active compound upon metabolism in the body, which may or may not be enzymatically controlled. Prodrugs may also be broadly classified into two groups: bioprecursor and carrier prodrugs. Prodrugs may also be subclassified according to the nature of their action. Bioprecursor prodrugs are compounds that already contain the embryo of the active species within their structure, whereby the active species are produced upon metabolism.

Carrier prodrugs are formed by combining the active drug with a carrier species forming a compound having desirable chemical and biological characteristics, whereby the link is an ester or amide so that the carrier prodrug is easily metabolized upon absorption or delivery to the target site. For example, lipophilic moieties may be incorporated to improve transport through membranes. Carrier prodrugs linked by a functional group to carrier are referred to as bipartite prodrugs. Prodrugs where the carrier is linked to the drug by a separate structure are referred to as tripartite prodrugs, whereby the carrier is removed by an enzyme-controlled metabolic process, and whereby the linking structure is removed by an enzyme system or by a chemical reaction.

A hydroxy-protecting group includes, for example, a tert-butyloxy-carbonyl (t-BOC) and t-butyl-dimethyl-silyl (TBS). Other hydroxy protecting groups contemplated are known in the art.

In another embodiment, a dosage form and/or composition may include one or more active metabolites of the active ingredients in place of or in addition to the active ingredients disclosed herein.

Dosage form compositions containing the active pharmaceutical ingredients may also contain one or more inactive pharmaceutical ingredients such as diluents, solubilizers, alcohols, binders, controlled release polymers, enteric polymers, disintegrants, excipients, colorants, flavorants, sweeteners, antioxidants, preservatives, pigments, additives, fillers, suspension agents, surfactants (for example, anionic, cationic, amphoteric and nonionic), and the like. Various FDA-approved topical inactive ingredients are found at the FDA's "The Inactive Ingredients Database" that contains inactive ingredients specifically intended as such by the manufacturer, whereby inactive ingredients can also be considered active ingredients under certain circumstances, according to the definition of an active ingredient given in 21 CFR 210.3(b)(7). Alcohol is a good example of an ingredient that may be considered either active or inactive depending on the product formulation.

As used herein, a kit may be a packaged collection of related materials, including, for example, a single and/or a plurality of dosage forms each approximating an effective amount of an active ingredient, such as, for example, an antipsychotic agent and/or a pharmaceutical compound that reverses or negates the effects of an NMDA receptor antagonist and/or an additional drug. The included dosage forms may be taken at one time, or at prescribed interval.

As used herein, an oral dosage form may include capsules (a solid oral dosage form consisting of a shell and a filling, whereby the shell is composed of a single sealed enclosure, or two halves that fit together and which are sometimes sealed with a band and whereby capsule shells may be made from gelatin, starch, or cellulose, or other suitable materials, may be soft or hard, and are filled with solid or liquid ingredients that can be poured or squeezed), capsule or coated pellets (solid dosage form in which the drug is enclosed within either a hard or soft soluble container or "shell" made from a suitable form of gelatin; the drug itself is in the form of granules to which varying amounts of coating have been applied), capsule coated extended release (a solid dosage form in which the drug is enclosed within either a hard or soft soluble container or "shell" made from a suitable form of gelatin; additionally, the capsule is covered in a designated coating, and which releases a drug or drugs in such a manner to allow at least a reduction in dosing frequency as compared to that drug or drugs presented as a conventional dosage form), capsule delayed release (a solid dosage form in which the drug is enclosed within either a hard or soft soluble container made from a suitable form of gelatin, and which releases a drug (or drugs) at a time other than promptly after administration, whereby enteric-coated articles are delayed release dosage forms), capsule delayed release pellets (solid dosage form in which the drug is enclosed within either a hard or soft soluble container or "shell" made from a suitable form of gelatin); the drug itself is in the form of granules to which enteric coating has been applied, thus delaying release of the drug until its passage into the intestines), capsule extended release (a solid dosage form in which the drug is enclosed within either a hard or soft soluble container made from a suitable form of gelatin, and which releases a drug or drugs in such a manner to allow a reduction in dosing frequency as compared to that drug or drugs presented as a conventional dosage form), capsule film-coated extended release (a solid dosage form in which the drug is enclosed within either a hard or soft soluble container or "shell" made from a suitable form of gelatin; additionally, the capsule is covered in a designated film coating, and which releases a drug or drugs in such a manner to allow at least a reduction in dosing frequency as compared to that drug or drugs presented as a conventional dosage form), capsule gelatin coated (a solid dosage form in which the drug is enclosed within either a hard or soft soluble container made from a suitable form of gelatin; through a banding process, the capsule is coated with additional layers of gelatin so as to form a complete seal), and capsule liquid filled (a solid dosage form in which the drug is enclosed within a soluble, gelatin shell which is plasticized by the addition of a polyol, such as sorbitol or glycerin, and is therefore of a somewhat thicker consistency than that of a hard shell capsule; typically, the active ingredients are dissolved or suspended in a liquid vehicle).

Oral dosage forms contemplated herein also include granules (a small particle or grain), pellet (a small sterile solid mass consisting of a highly purified drug, with or without excipients, made by the formation of granules, or by compression and molding), pellets coated extended release (a solid dosage form in which the drug itself is in the form of granules to which varying amounts of coating have been applied, and which releases a drug or drugs in such a manner to allow a reduction in dosing frequency as compared to that drug or drugs presented as a conventional dosage form), pill (a small, round solid dosage form containing a medicinal agent intended for oral administration), powder (an intimate mixture of dry, finely divided drugs and/or chemicals that may be intended for internal or external use), elixir (a clear, pleasantly flavored, sweetened hydroalcoholic liquid containing dissolved medicinal agents; it is intended for oral use), chewing gum (a sweetened and flavored insoluble plastic material of various shapes which when chewed, releases a drug substance into the oral cavity), or syrup (an oral solution containing high concentrations of sucrose or other sugars; the term has also been used to include any other liquid dosage form prepared in a sweet and viscid vehicle, including oral suspensions).

Oral dosage forms contemplated herein may further include a tablet (a solid dosage form containing medicinal substances with or without suitable diluents), tablet chewable (a solid dosage form containing medicinal substances with or without suitable diluents that is intended to be chewed, producing a pleasant tasting residue in the oral cavity that is easily swallowed and does not leave a bitter or unpleasant after-taste), tablet coated (a solid dosage form that contains medicinal substances with or without suitable diluents and is covered with a designated coating), tablet coated particles (a solid dosage form containing a conglomerate of medicinal particles that have each been covered with a coating), tablet delayed release (a solid dosage form which releases a drug or drugs at a time other than promptly after administration, whereby enteric-coated articles are delayed release dosage forms), tablet delayed release particles (a solid dosage form containing a conglomerate of medicinal particles that have been covered with a coating which releases a drug or drugs at a time other than promptly after administration, whereby enteric-coated articles are delayed release dosage forms), tablet dispersible (a tablet that, prior to administration, is intended to be placed in liquid, where its contents will be distributed evenly throughout that liquid, whereby term 'tablet, dispersible' is no longer used for approved drug products, and it has been replaced by the term 'tablet, for suspension'), tablet effervescent (a solid dosage form containing mixtures of acids, for example, citric acid, tartaric acid, and sodium bicarbonate, which release carbon dioxide when dissolved in water, whereby it is intended to be dissolved or dispersed in water before administration), tablet extended release (a solid dosage form containing a drug which allows at least a reduction in dosing frequency as compared to that drug presented in conventional dosage form), tablet film coated (a solid dosage form that contains medicinal substances with or without suitable diluents and is coated with a thin layer of a water-insoluble or water-soluble polymer), tablet film coated extended release (a solid dosage form that contains medicinal substances with or without suitable diluents and is coated with a thin layer of a water-insoluble or water-soluble polymer; the tablet is formulated in such manner as to make the contained medicament available over an extended period of time following ingestion), tablet for solution (a tablet that forms a solution when placed in a liquid), tablet for suspension (a tablet that forms a suspension when placed in a liquid, which is formerly referred to as a 'dispersible tablet'), tablet multilayer (a solid dosage form containing medicinal substances that have been compressed to form a multiple-layered tablet or a tablet-within-a-tablet, the inner tablet being the core and the outer portion being the shell), tablet multilayer extended release (a solid dosage form containing medicinal substances that have been compressed to form a multiple-layered tablet or a tablet-within-a-tablet, the inner tablet being the core and the outer portion being the shell, which, additionally, is covered in a designated coating; the tablet is formulated in such manner as to allow at least a reduction in dosing frequency as compared to that drug presented as a conventional dosage form), tablet orally disintegrating (a solid dosage form containing medicinal substances which disintegrates rapidly, usually within a matter of seconds, when placed upon the tongue), tablet orally disintegrating delayed release (a solid dosage form containing medicinal substances which disintegrates rapidly, usually within a matter of seconds, when placed upon the tongue, but which releases a drug or drugs at a time other than promptly after administration), tablet soluble (a solid dosage form that contains medicinal substances with or without suitable diluents and possesses the ability to dissolve in fluids), tablet sugar coated (a solid dosage form that contains medicinal substances with or without suitable diluents and is coated with a colored or an uncolored water-soluble sugar), and the like.

Injection and infusion dosage forms (i.e., parenteral dosage forms) include, but are not limited to, the following. Liposomal injection includes or forms liposomes or a lipid bilayer vesicle having phospholipids that encapsulate an active drug substance. Injection includes a sterile preparation intended for parenteral use. Five distinct classes of injections exist as defined by the USP. Emulsion injection includes an emulsion comprising a sterile, pyrogen-free preparation intended to be administered parenterally. Lipid complex and powder for solution injection are sterile preparations intended for reconstitution to form a solution for parenteral use.

Powder for suspension injection is a sterile preparation intended for reconstitution to form a suspension for parenteral use. Powder lyophilized for liposomal suspension injection is a sterile freeze dried preparation intended for reconstitution for parenteral use that is formulated in a manner allowing incorporation of liposomes, such as a lipid bilayer vesicle having phospholipids used to encapsulate an active drug substance within a lipid bilayer or in an aqueous space, whereby the formulation may be formed upon reconstitution. Powder lyophilized for solution injection is a dosage form intended for the solution prepared by lyophilization ("freeze drying"), whereby the process involves removing water from products in a frozen state at extremely low pressures, and whereby subsequent addition of liquid creates a solution that conforms in all respects to the requirements for injections. Powder lyophilized for suspension injection is a liquid preparation intended for parenteral use that contains solids suspended in a suitable fluid medium, and it conforms in all respects to the requirements for Sterile Suspensions, whereby the medicinal agents intended for the suspension are prepared by lyophilization.

Solution injection involves a liquid preparation containing one or more drug substances dissolved in a suitable solvent or mixture of mutually miscible solvents that is suitable for injection. Solution concentrate injection involves a sterile preparation for parenteral use that, upon addition of suitable solvents, yields a solution suitable for injections. Suspension injection involves a liquid preparation (suitable for injection) containing solid particles dispersed throughout a liquid phase, whereby the particles are insoluble, and whereby an oil phase is dispersed throughout an aqueous phase or vice-versa. Suspension liposomal injection is a liquid preparation (suitable for injection) having an oil phase dispersed throughout an aqueous phase in such a manner that liposomes (a lipid bilayer vesicle usually containing phospholipids used to encapsulate an active drug substance either within a lipid bilayer or in an aqueous space) are formed. Suspension sonicated injection is a liquid preparation (suitable for injection) containing solid particles dispersed throughout a liquid phase, whereby the particles are insoluble. In addition, the product may be sonicated as a gas is bubbled through the suspension resulting in the formation of microspheres by the solid particles.

A parenteral carrier system may include one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives.

Inhalation dosage forms include, but are not limited to, aerosol being a product that is packaged under pressure and contains therapeutically active ingredients that are released upon activation of an appropriate valve system intended for topical application to the skin as well as local application into the nose (nasal aerosols), mouth (lingual and sublingual aerosols), or lungs (inhalation aerosols). Inhalation dosage forms further include foam aerosol being a dosage form containing one or more active ingredients, surfactants, aqueous or non-aqueous liquids, and the propellants, whereby if the propellant is in the internal (discontinuous) phase (i.e., of the oil-in-water type), a stable foam is discharged, and if the propellant is in the external (continuous) phase (i.e., of the water-in-oil type), a spray or a quick-breaking foam is discharged Inhalation dosage forms also include metered aerosol being a pressurized dosage form consisting of metered dose valves which allow for the delivery of a uniform quantity of spray upon each activation; powder aerosol being a product that is packaged under pressure and contains therapeutically active ingredients, in the form of a powder, that are released upon activation of an appropriate valve system; and aerosol spray being an aerosol product which utilizes a compressed gas as the propellant to provide the force necessary to expel the product as a wet spray and being applicable to solutions of medicinal agents in aqueous solvents.

Pharmaceutically suitable inhalation carrier systems may include pharmaceutically suitable inactive ingredients known in the art for use in various inhalation dosage forms, such as (but not limited to) aerosol propellants (for example, hydrofluoroalkane propellants), surfactants, additives, suspension agents, solvents, stabilizers and the like.

A transdermal dosage form may include, but is not limited to, a patch being a drug delivery system that often contains an adhesive backing that is usually applied to an external site on the body, whereby the ingredients either passively diffuse from, or are actively transported from some portion of the patch, and whereby depending upon the patch, the ingredients are either delivered to the outer surface of the body or into the body; and other various types of transdermal patches such as matrix, reservoir and others known in the art. The "pharmaceutically suitable transdermal carrier system" includes pharmaceutically suitable inactive ingredients known in the art for use in various transdermal dosage forms, such as (but not limited to) solvents, adhesives, diluents, additives, permeation enhancing agents, surfactants, emulsifiers, liposomes, and the like.

Suitable dosage amounts and dosing regimens may be selected in accordance with a variety of factors, including one or more particular conditions being treated, the severity of the one or more conditions, the genetic profile, age, health, sex, diet, and weight of the subject, the route of administration alone or in combination with pharmacological considerations including the activity, efficacy, bioavailability, pharmacokinetic, and toxicological profiles of the particular compound employed, whether a drug delivery system is utilized and whether the drug is administered as part of a drug combination. Therefore, the dosage regimen to be employed may vary widely and may necessarily deviate from the dosage regimens set forth herein.

Contemplated dosage forms may include an amount of one or more antipsychotic agents ranging from about 1 to about 1200 mg, or about 5 to about 100 mg, or about 25 to about 800 mg, or about 100 to about 500 mg, or 0.1 to 50 milligrams (±10%), or 10 to 100 milligrams (±10%), or 5 to 500 milligrams (±10%), or 0.1 to 200 milligrams (±10%), or 1 to 100 milligrams (±10%), or 5 to 50 milligrams (±10%), or 30 milligrams (±10%), or 20 milligrams (±10%), or 10 milligrams (±10%), or 5 milligrams (±10%), per dosage form, such as, for example, a tablet, a pill, a bolus, and the like.

Contemplated dosage forms may include an amount of one or more compounds that reverse or negate the effects of an NMDA receptor antagonist ranging from about 1 to about 1200 mg, or about 5 to about 100 mg, or about 25 to about 800 mg, or about 25 to about 60 mg, or about 100 to about 500 mg, or 0.1 to 50 milligrams (±10%), or 10 to 100 milligrams (±10%), or 5 to 500 milligrams (±10%), or 0.1 to 200 milligrams (±10%), or 1 to 100 milligrams (±10%), or 5 to 50 milligrams (±10%), or 30 milligrams (±10%), or 20 milligrams (±10%), or 10 milligrams (±10%), or 5 milligrams (±10%), per dosage form, such as, for example, a tablet, a pill, a bolus, and the like.

Contemplated dosage forms may include an amount of one or more benzodiazepines ranging from 10 milligrams (±10%), or 5 milligrams (±10%), or 2 milligrams (±10%), or 1 milligram (±10%), or 500 micrograms (±10%), or 100 micrograms (±10%), 30 micrograms (±10%) per dosage form, or 20 micrograms (±10%), or 10 micrograms (±10%), or 5 micrograms (±10%), or 0.1 to 50 micrograms (±10%), or about 500 to about 10,000 μg, or 10 to 100 micrograms (±10%), or 5 to 500 micrograms (±10%), or 0.1 to 200 micrograms (±10%), or 1 to 100 micrograms (±10%), or 5 to 50 micrograms (±10%) per dosage form, such as, for example, a tablet, a pill, a bolus, and the like. In one embodiment, a subject may receive between about one milligram to about 6 milligrams total per day or more or less.

In one example, a subject may receive between 0.1 and 200 milligrams/kg (±10%) of each active ingredient every 4-6 hours at the same or different times or more often or less often to achieve maximal benefit per subject.

For example, an antipsychotic agent may be included in an amount of 10 milligrams (±10%) in one dosage form. Further, the antipsychotic may be combined with a pharmaceutical compound that reverses or negates the effects of an NMDA receptor antagonist in a single dosage form in an amount of 100 milligrams (±10%), or 50 milligrams (±10%), or 20 milligrams (±10%), or 1 to 30 milligrams (±10%), or 4 to 60 milligrams (±10%), or 10 to 500 milligrams (±10%) per dose. Similarly, a dosage form may include a pharmaceutical compound that reverse or negate the effects of an NMDA receptor antagonist by itself or in combination with an antipsychotic agent or other agent for which improved cognition may be observed, in an amount of 100 milligrams (±10%), or 50 milligrams (±10%), or 20 milligrams (±10%), or 1-30 milligrams (±10%), or 4 to 60 milligrams (±10%), or 10 to 500 milligrams (±10%) per dose.

In another embodiment, a dosage form may be administered to a subject in need thereof once per day, or twice per day, or once every 6 hours, or once every 4 hours, or once every 2 hours, or hourly, or twice an hour, or twice a day, or twice a week, or monthly. A therapeutically effective amount of a pharmaceutical compound that reverses or negates the effects of an NMDA receptor antagonist or mimic thereof, such as, for example, lamotrigine, may be any amount that begins to reduce catatonic features in a subject receiving the compound. For example, an effective amount of lamotrigine is an amount the reduces a subject's Bush-Francis Catatonia Rating Scale score (discussed herein below). In another example, an effective amount of a pharmaceutical compound that reverses or negates the effects of an NMDA receptor antagonist or mimic thereof, for example, may be about 5 mg, or about 10 mg, or about 25 mg, or about 50 mg, or about 100 mg, or about 200 mg, or about 400 mg, or about 500 mg, or about 600 mg, or from about 10 to about 60 mg, or about 50 mg to about 200 mg, or about 150 mg to about 600 mg per day. Further, an effective amount may be about 200 mg of lamotrigine or a mimic thereof administered twice a day.

A therapeutically effective amount of an antipsychotic agent may be any amount that begins to improve a psychotic disorder in a subject. In one embodiment, an effective amount of an antipsychotic agent used in the therapeutic regime described herein may be, for example, about 1 mg, or about 5 mg, or about 10 mg, or about 25 mg, or about 50 mg, or about 100 mg, or about 200 mg, or about 400 mg, or about 500 mg, or about 600 mg, or about 1000 mg, or about 1200 mg, or about 1400 mg, or from about 10 to about 60 mg, or about 50 mg to about 200 mg, or about 150 mg to about 600 mg per day. Further, another effective amount of an antipsychotic agent used herein may be that which results in a detectable blood level of above about 35 ng/dL, or about 70 ng/dL, or about 140 ng/dL, or about 280 ng/dL, or about 350 ng/dL, or higher.

Without wishing to be bound by theory, it is believed that administration of a pharmaceutical compound that reverses or negates the effects of an NMDA receptor antagonist or mimic thereof, in combination with an antipsychotic agent may lead to a decrease in the required dosage of at least one of the pharmaceutical compound that reverses or negates the effects of an NMDA receptor antagonist or mimic thereof or the antipsychotic agent. In this way, the combined therapy may lead to reduced overall drug intake and a diminution of drug-associated detrimental sequelae.

It is further contemplated that one active ingredient may be in an extended release form, while a second other may not be, so the recipient experiences, for example, a spike in the second active ingredient that dissipates rapidly, while the first active ingredient is maintained in a higher concentration in the blood stream over a longer period of time. Similarly, one of the active ingredients may be an active metabolite, while another may be in an unmetabolized state, such that the active metabolite has an immediate effect upon administration to a subject whereas the unmetabolized active ingredient administered in a single dosage form may need to be metabolized before taking effect in the subject.

Also contemplated are solid form preparations that include at least one active ingredient which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Solutions or suspensions may be applied topically and/or directly to the nasal cavity, respiratory tract, eye, or ear by conventional means, for example with a dropper, pipette or spray.

Alternatively, one or more of the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier may form a gel in the nasal cavity. The powder composition may be presented in unit dose form, for example, in capsules or cartridges of, for example, gelatin, or blister packs from which the powder may be administered by means of an inhaler.

The pharmaceutical preparations may be in unit dosage forms. In such form, the preparation may be subdivided into unit doses containing appropriate quantities of the active component. The unit dosage form can be a packaged preparation, such as a kit or other form, the package containing discrete quantities of preparation, such as packeted tablets, capsules, liquids or powders in vials or ampoules. Also, the unit dosage form can be a capsule, tablet, cachet, or lozenge, or it can be the appropriate number of any of these in packaged form. Contemplated kits may include any combination of disclosed dosage forms.

EXAMPLES

In cataloging the beneficial behavioral changes associated with a reduction in catatonic features, it is important to note that multiple domains can be assessed with the Bush-Francis Catatonia Rating Scale (BFCRS) (Bush, G., Fink, M., Petrides, G., et at (1996) Catatonia. I. Rating scale and standardized examination. *Acta Psychiatrica Scandinavica*, 93, 129-136). This assessment tool, in conjunction with clinical observation, can be used to identify the severity of catatonia and track improvements with medication adjustments. Studies discussed herein focused on subjects in both secure and nonsecure residential settings. Accordingly, the beneficial treatment responses that were initially observed in secure settings were subsequently observed in nonsecure settings using the same methodological and clinical approaches to diagnosis and treatment. Treatment-dependent improvements in patient BFCRS scores are provided in Tables No. 1A-D below. The patients A-L included in Tables No. 1A and 1B did not receive a benzodiazepine, whereas patients M-X included in Tables No. 1C and 1D did receive a benzodiazepine. The medications of the patients at the time of post-treatment assessment are indicated in Table No. 2.

TABLE NO. 1A

Treatment-dependent Reduction in Catatonic Features in Patients

| Behavior | Patient A | | Patient B | | Patient C | | Patient D | | Patient E | | Patient F | |
|---|---|---|---|---|---|---|---|---|---|---|---|---|
| | Pre | Post | Pre | Post | Pre | Post | Pre | Post | Pre | Post | Pre | Post |
| Excitement[a] | 0 | 0 | 0 | 0 | 0 | 0 | 0 | 0 | 1 | 0 | 0 | 0 |
| Immobility/stupor[b] | 1 | 1 | 0 | 0 | 0 | 0 | 1 | 1 | 0 | 0 | 1 | 1 |
| Mutism[c] | 2 | 1 | 0 | 0 | 0 | 0 | 0 | 0 | 0 | 0 | 2 | 1 |
| Staring[d] | 1 | 1 | 0 | 0 | 0 | 0 | 1 | 1 | 1 | 0 | 1 | 0 |
| Posturing/catalepsy[e] | 2 | 1 | 1 | 1 | 3 | 0 | 2 | 1 | 0 | 0 | 0 | 0 |
| Grimacing[f] | 0 | 0 | 0 | 0 | 2 | 0 | 0 | 0 | 0 | 0 | 1 | 0 |
| Echopraxia/echolalia[g] | 0 | 0 | 0 | 0 | 0 | 0 | 0 | 0 | 1 | 1 | 0 | 0 |
| Stereotypy[h] | 0 | 0 | 2 | 1 | 1 | 0 | 2 | 1 | 2 | 1 | 0 | 0 |
| Mannerisms[i] | 0 | 0 | 0 | 0 | 1 | 0 | 0 | 0 | 0 | 0 | 0 | 0 |
| Verbigeration[j] | 0 | 0 | 0 | 0 | 0 | 0 | 0 | 0 | 3 | 1 | 0 | 0 |
| Rigidity[k] | 0 | 0 | 0 | 0 | 0 | 0 | 0 | 0 | 0 | 0 | 0 | 0 |
| Negativism[l] | 0 | 0 | 2 | 1 | 0 | 0 | 1 | 1 | 2 | 1 | 0 | 0 |
| Waxy flexibility[m] | 0 | 0 | 0 | 0 | 0 | 0 | 0 | 0 | 0 | 0 | 0 | 0 |
| Withdrawal[n] | 2 | 1 | 0 | 0 | 0 | 0 | 0 | 0 | 1 | 1 | 1 | 1 |
| Impulsivity[o] | 0 | 0 | 2 | 1 | 2 | 0 | 0 | 0 | 1 | 1 | 0 | 0 |
| Automatic obedience[p] | 0 | 0 | 0 | 0 | 0 | 0 | 0 | 0 | 2 | 1 | 0 | 0 |
| Mitegehen[q] | 0 | 0 | 0 | 0 | 0 | 0 | 0 | 0 | 3 | 3 | 3 | 0 |
| Gegenhalten[r] | 0 | 0 | 0 | 0 | 0 | 0 | 0 | 0 | 0 | 0 | 0 | 0 |
| Ambitendency[s] | 3 | 0 | 0 | 0 | 3 | 0 | 3 | 0 | 0 | 0 | 0 | 0 |
| Grasp reflex[t] | 0 | 0 | 0 | 0 | 0 | 0 | 0 | 0 | 0 | 0 | 0 | 0 |
| Perseveration[u] | 0 | 0 | 3 | 0 | 0 | 0 | 3 | 3 | 3 | 3 | 0 | 0 |
| Combativeness[v] | 0 | 0 | 0 | 0 | 0 | 0 | 0 | 0 | 0 | 0 | 0 | 0 |
| Autonomic abnormality[w] | 0 | 0 | 0 | 0 | 0 | 0 | 0 | 0 | 0 | 0 | 0 | 0 |
| TOTAL | 11 | 5 | 10 | 4 | 12 | 0 | 13 | 8 | 20 | 13 | 9 | 3 |

TABLE NO. 1B

Treatment-dependent Reduction in Catatonic Features in Patients

| Behavior | Patient G | | Patient H | | Patient I | | Patient J | | Patient K | | Patient L | |
|---|---|---|---|---|---|---|---|---|---|---|---|---|
| | Pre | Post | Pre | Post | Pre | Post | Pre | Post | Pre | Post | Pre | Post |
| Excitement[a] | 0 | 0 | 0 | 0 | 0 | 0 | 2 | 0 | 0 | 0 | 1 | 0 |
| Immobility/stupor[b] | 1 | 0 | 2 | 1 | 1 | 0 | 0 | 0 | 2 | 1 | 0 | 0 |
| Mutism[c] | 0 | 0 | 2 | 1 | 0 | 0 | 0 | 0 | 2 | 0 | 1 | 0 |
| Staring[d] | 0 | 0 | 1 | 0 | 1 | 0 | 2 | 0 | 2 | 0 | 0 | 0 |
| Posturing/catalepsy[e] | 2 | 0 | 3 | 0 | 1 | 0 | 3 | 0 | 2 | 0 | 0 | 0 |
| Grimacing[f] | 0 | 0 | 0 | 0 | 2 | 0 | 0 | 0 | 0 | 0 | 1 | 0 |
| Echopraxia/echolalia[g] | 0 | 0 | 0 | 0 | 0 | 0 | 0 | 0 | 0 | 0 | 0 | 0 |
| Stereotypy[h] | 1 | 0 | 0 | 0 | 0 | 0 | 2 | 1 | 0 | 0 | 1 | 0 |
| Mannerisms[i] | 0 | 0 | 0 | 0 | 1 | 0 | 0 | 0 | 0 | 0 | 0 | 0 |
| Verbigeration[j] | 0 | 0 | 2 | 1 | 0 | 0 | 2 | 0 | 1 | 1 | 1 | 0 |
| Rigidity[k] | 0 | 0 | 1 | 1 | 0 | 0 | 0 | 0 | 0 | 0 | 0 | 0 |
| Negativism[l] | 2 | 0 | 2 | 1 | 2 | 0 | 0 | 0 | 3 | 1 | 1 | 0 |
| Waxy flexibility[m] | 0 | 0 | 0 | 0 | 0 | 0 | 0 | 0 | 0 | 0 | 0 | 0 |
| Withdrawal[n] | 2 | 1 | 3 | 0 | 0 | 0 | 2 | 0 | 2 | 1 | 0 | 0 |
| Impulsivity[o] | 0 | 0 | 0 | 0 | 2 | 0 | 0 | 0 | 0 | 0 | 1 | 0 |
| Automatic obedience[p] | 3 | 0 | 1 | 1 | 1 | 0 | 0 | 0 | 0 | 0 | 1 | 1 |
| Mitegehen[q] | 0 | 0 | 3 | 3 | 3 | 0 | 3 | 0 | 0 | 0 | 3 | 0 |
| Gegenhalten[r] | 0 | 0 | 0 | 0 | 0 | 0 | 0 | 0 | 0 | 0 | 0 | 0 |

TABLE NO. 1B-continued

Treatment-dependent Reduction in Catatonic Features in Patients

| Behavior | Patient G Pre | Patient G Post | Patient H Pre | Patient H Post | Patient I Pre | Patient I Post | Patient J Pre | Patient J Post | Patient K Pre | Patient K Post | Patient L Pre | Patient L Post |
|---|---|---|---|---|---|---|---|---|---|---|---|---|
| Ambitendency[s] | 0 | 0 | 0 | 0 | 3 | 0 | 3 | 0 | 3 | 0 | 3 | 3 |
| Grasp reflex[t] | 0 | 0 | 0 | 0 | 0 | 0 | 0 | 0 | 0 | 0 | 0 | 0 |
| Perseveration[u] | 0 | 0 | 3 | 3 | 0 | 0 | 3 | 3 | 3 | 3 | 3 | 3 |
| Combativeness[v] | 0 | 0 | 1 | 1 | 0 | 0 | 0 | 0 | 1 | 0 | 0 | 0 |
| Autonomic abnormality[w] | 0 | 0 | 0 | 0 | 0 | 0 | 0 | 0 | 0 | 0 | 0 | 0 |
| TOTAL | 11 | 1 | 24 | 13 | 17 | 0 | 22 | 4 | 21 | 7 | 17 | 7 |

TABLE NO. 1C

Treatment-dependent Reduction in Catatonic Features in Patients

| Behavior | Patient M Pre | Patient M Post | Patient N Pre | Patient N Post | Patient O Pre | Patient O Post | Patient P Pre | Patient P Post | Patient Q Pre | Patient Q Post | Patient R Pre | Patient R Post |
|---|---|---|---|---|---|---|---|---|---|---|---|---|
| Excitement[a] | 0 | 0 | 1 | 0 | 0 | 0 | 0 | 0 | 1 | 0 | 1 | 0 |
| Immobility/stupor[b] | 1 | 0 | 0 | 0 | 2 | 1 | 1 | 0 | 1 | 0 | 0 | 0 |
| Mutism[c] | 2 | 0 | 0 | 0 | 3 | 1 | 2 | 0 | 1 | 0 | 1 | 0 |
| Staring[d] | 1 | 0 | 1 | 0 | 2 | 0 | 1 | 0 | 3 | 0 | 0 | 0 |
| Posturing/catalepsy[e] | 3 | 0 | 0 | 0 | 2 | 1 | 1 | 0 | 3 | 0 | 3 | 0 |
| Grimacing[f] | 0 | 0 | 1 | 0 | 0 | 0 | 1 | 0 | 0 | 0 | 2 | 1 |
| Echopraxia/echolalia[g] | 0 | 0 | 0 | 0 | 0 | 0 | 0 | 0 | 0 | 0 | 0 | 0 |
| Stereotypy[h] | 0 | 0 | 3 | 1 | 0 | 0 | 1 | 0 | 0 | 0 | 0 | 0 |
| Mannerisms[i] | 0 | 0 | 0 | 0 | 1 | 0 | 0 | 0 | 2 | 1 | 2 | 0 |
| Verbigeration[j] | 1 | 0 | 2 | 0 | 0 | 0 | 1 | 0 | 1 | 0 | 0 | 0 |
| Rigidity[k] | 0 | 0 | 0 | 0 | 0 | 0 | 0 | 0 | 0 | 0 | 0 | 0 |
| Negativism[l] | 2 | 1 | 2 | 0 | 2 | 1 | 1 | 0 | 2 | 0 | 2 | 1 |
| Waxy flexibility[m] | 0 | 0 | 0 | 0 | 0 | 0 | 0 | 0 | 0 | 0 | 0 | 0 |
| Withdrawal[n] | 3 | 0 | 0 | 0 | 1 | 0 | 2 | 0 | 1 | 0 | 0 | 0 |
| Impulsivity[o] | 0 | 0 | 2 | 0 | 0 | 0 | 1 | 0 | 3 | 1 | 2 | 0 |
| Automatic obedience[p] | 0 | 0 | 0 | 0 | 0 | 0 | 0 | 0 | 0 | 0 | 0 | 0 |
| Mitegehen[q] | 3 | 0 | 3 | 0 | 3 | 0 | 3 | 0 | 0 | 0 | 0 | 0 |
| Gegenhalten[r] | 0 | 0 | 0 | 0 | 0 | 0 | 0 | 0 | 0 | 0 | 0 | 0 |
| Ambitendency[s] | 0 | 0 | 0 | 0 | 0 | 0 | 3 | 0 | 0 | 0 | 0 | 0 |
| Grasp reflex[t] | 0 | 0 | 0 | 0 | 0 | 0 | 1 | 0 | 0 | 0 | 0 | 0 |
| Perseveration[u] | 0 | 0 | 3 | 3 | 0 | 0 | 3 | 0 | 3 | 0 | 0 | 0 |
| Combativeness[v] | 0 | 0 | 2 | 0 | 0 | 0 | 2 | 1 | 0 | 0 | 3 | 0 |
| Autonomic abnormality[w] | 0 | 0 | 0 | 0 | 0 | 0 | 0 | 0 | 0 | 0 | 0 | 0 |
| TOTAL | 16 | 1 | 20 | 4 | 16 | 4 | 24 | 1 | 21 | 2 | 16 | 2 |

TABLE NO. 1D

Treatment-dependent Reduction in Catatonic Features in Patients

| Behavior | Patient S Pre | Patient S Post | Patient T Pre | Patient T Post | Patient U Pre | Patient U Post | Patient V Pre | Patient V Post | Patient W Pre | Patient W Post | Patient X Pre | Patient X Post |
|---|---|---|---|---|---|---|---|---|---|---|---|---|
| Excitement[a] | 0 | 0 | 2 | 1 | 1 | 0 | 1 | 0 | 0 | 0 | 2 | 0 |
| Immobility/stupor[b] | 2 | 0 | 2 | 0 | 0 | 0 | 0 | 0 | 2 | 1 | 0 | 0 |
| Mutism[c] | 2 | 0 | 1 | 0 | 1 | 0 | 1 | 0 | 2 | 0 | 0 | 0 |
| Staring[d] | 3 | 0 | 2 | 1 | 0 | 0 | 0 | 0 | 1 | 0 | 2 | 0 |
| Posturing/catalepsy[e] | 3 | 0 | 1 | 0 | 0 | 0 | 1 | 0 | 2 | 0 | 0 | 0 |
| Grimacing[f] | 1 | 0 | 0 | 0 | 0 | 0 | 0 | 0 | 0 | 0 | 2 | 0 |
| Echopraxia/echolalia[g] | 0 | 0 | 0 | 0 | 0 | 0 | 0 | 0 | 0 | 0 | 1 | 0 |
| Stereotypy[h] | 0 | 0 | 0 | 0 | 2 | 1 | 0 | 0 | 1 | 0 | 3 | 0 |
| Mannerisms[i] | 0 | 0 | 0 | 0 | 0 | 0 | 0 | 0 | 1 | 0 | 2 | 0 |
| Verbigeration[j] | 2 | 0 | 2 | 1 | 2 | 0 | 3 | 2 | 0 | 0 | 3 | 1 |
| Rigidity[k] | 1 | 0 | 0 | 0 | 0 | 0 | 1 | 0 | 1 | 0 | 0 | 0 |
| Negativism[l] | 1 | 0 | 2 | 1 | 1 | 0 | 1 | 0 | 2 | 1 | 2 | 0 |
| Waxy flexibility[m] | 0 | 0 | 0 | 0 | 0 | 0 | 0 | 0 | 0 | 0 | 0 | 0 |
| Withdrawal[n] | 3 | 0 | 1 | 0 | 1 | 0 | 2 | 0 | 1 | 0 | 0 | 0 |
| Impulsivity[o] | 0 | 0 | 0 | 0 | 1 | 0 | 1 | 1 | 0 | 0 | 3 | 0 |
| Automatic obedience[p] | 0 | 0 | 0 | 0 | 0 | 0 | 0 | 0 | 0 | 0 | 0 | 0 |
| Mitegehen[q] | 3 | 0 | 3 | 0 | 3 | 0 | 3 | 0 | 3 | 0 | 3 | 0 |

TABLE NO. 1D-continued

Treatment-dependent Reduction in Catatonic Features in Patients

| Behavior | Patient S Pre | Patient S Post | Patient T Pre | Patient T Post | Patient U Pre | Patient U Post | Patient V Pre | Patient V Post | Patient W Pre | Patient W Post | Patient X Pre | Patient X Post |
|---|---|---|---|---|---|---|---|---|---|---|---|---|
| Gegenhalten[r] | 3 | 0 | 0 | 0 | 0 | 0 | 0 | 0 | 0 | 0 | 0 | 0 |
| Ambitendency[s] | 3 | 0 | 0 | 0 | 0 | 0 | 3 | 0 | 0 | 0 | 3 | 0 |
| Grasp reflex[t] | 0 | 0 | 0 | 0 | 0 | 0 | 1 | 0 | 0 | 0 | 0 | 0 |
| Perseveration[u] | 3 | 0 | 3 | 3 | 3 | 3 | 3 | 3 | 0 | 0 | 3 | 3 |
| Combativeness[v] | 0 | 0 | 0 | 0 | 0 | 0 | 0 | 0 | 0 | 0 | 1 | 0 |
| Autonomic abnormality[w] | 1 | 0 | 0 | 0 | 0 | 0 | 1 | 0 | 0 | 0 | 0 | 0 |
| TOTAL | 31 | 0 | 19 | 7 | 15 | 4 | 22 | 6 | 16 | 2 | 30 | 4 |

[a]Extreme hyperactivity, constant motor unrest which is apparently nonpurposeful. Not to be attributed to akathisia or goal directed agitation - scale = 0-3, where 0 = absent and 3 = constant or not redirectable;
[b]Extreme hypoactivity, immobile, minimally responsive to stimuli - scale = 0-3, where 0 = absent and 3 = stuporous, non-reactive to painful stimuli;
[c]Verbally unresponsive or minimally responsive - scale = 0-3, where 0 = absent and 3 = no speech;
[d]Fixed gaze, little or no visual scanning of environment, decreased blinking - scale = 0-3, where 0 = absent and 3 = fixed gaze, non-reactive;
[e]Spontaneous maintenance of posture(s), including mundane (e.g. setting or standing for long periods without reacting) - scale = 0-3, where 0 = absent and 3 = bizarre posture, or mundane maintained more than 15 minutes;
[f]Maintenance of odd facial expressions - scale = 0-3, where 0 = absent and 3 = bizarre expression(s) or maintained more than 1 minute;
[g]Mimicking of examiner's movements/speech - scale = 0-3, where 0 = absent and 3 = constant;
[h]Repetitive, non-goal-directed motor activity (e.g. finger-play; repeatedly touching, patting or rubbing self); abnormality not inherent in act but in frequency - scale = 0-3, where 0 = absent and 3 = constant;
[i]Odd, purposeful movements (hopping or walking tiptoe, saluting passersby or exaggerated caricatures of mundane movements); abnormality inherent in act itself - scale = 0-3, where 0 = absent and 3 = constant;
[j]Repetition of phrases or sentences (like a scratched record) - scale = 0-3, where 0 = absent and 3 = constant;
[k]Maintenance of a rigid position despite efforts to be moved, exclude if cogwheeling or tremor present - scale = 0-3, where 0 = absent and 3 = severe, cannot be repostured;
[l]Apparently motiveless resistance to instructions or attempts to move/examine patient. Contrary behavior, does exact opposite of instruction - scale = 0-3, where 0 = absent and 3 = severe resistance and/or continually contrary;
[m]During reposturing of patient, patient offers initial resistance before allowing himself to be repositioned, similar to that of a bending candle - scale = 0-3, where 0 = absent and 3 = present;
[n]Refusal to eat, drink and/or make eye contact - scale = 0-3, where 0 = absent and 3 = no PO intake/interaction for 1 day or more;
[o]Patient suddenly engages in inappropriate behavior (e.g. runs down hallway, starts screaming or takes off clothes) without provocation. Afterwards can give no, or only a facile explanation - scale = 0-3, where 0 = absent and 3 = constant or not redirectable;
[p]Exaggerated cooperation with examiner's request or spontaneous continuation of movement requested - scale = 0-3, where 0 = absent and 3 = constant;
[q]"Anglepoise lamp" arm raising in response to light pressure of finger, despite instruction to the contrary - scale = 0-3, where 0 = absent and 3 = present;
[r]Resistance to passive movement which is proportional to strength of the stimulus, appears automatic rather than willful - scale = 0-3, where 0 = absent and 3 = present;
[s]Patient appears motorically "stuck" in indecisive, hesitant movement - scale = 0-3, where 0 = absent and 3 = present;
[t]Per neurological exam - scale = 0-3, where 0 = absent and 3 = present;
[u]Repeatedly returns to same topic or persists with movement - scale = 0-3, where 0 = absent and 3 = present;
[v]Usually in an undirected manner, with no, or only a facile explanation afterwards - scale = 0-3, where 0 = absent and 3 = serious danger to others;
[w]Circle: temperature, BP, pulse, respiratory rate, diaphoresis - scale = 0-3, where 0 = absent and 3 = abnormality of three or more parameters;

TABLE NO. 2

Patient treatment plan at time of second BFCRS examination.

| Patient | Daily Dosage of Lamotrigine | Dosage of Antipsychotic | Dosage of Benzodiazepine | Length of treatment |
|---|---|---|---|---|
| Patient A | 50 mg | Abilify ® (aripipazole) 15 mg | 0 | 3 weeks |
| Patient B | 50 mg | Trilafon ® (perphenazine) 32 mg | 0 | 3 weeks |
| Patient C | 225 mg | Olanzapine 30 mg | 0 | >6 months |
| Patient D | 25 mg | Clozapine 600 mg | 0 | <2 weeks |
| Patient E | 75 mg | Risperdal ® consta ® (risperdone) 50 mg IM q 2 weeks | 0 | 5 weeks |
| Patient F | 100 mg | Clozapine 600 mg | 0 | 2 months |
| Patient G | 200 mg | Risperdal ® consta ® (risperdone) 50 mg IM q 2 weeks | 0 | 4 months |
| Patient H | 275 mg | Olanzapine 27.5 mg | 0 | >6 months |
| Patient I | 200 mg | Clozapine 150 mg | 0 | >6 months |
| Patient J | 150 mg | Olanzapine 40 mg | 0 | >6 months |
| Patient K | 400 mg | Clozapine 575 mg | 0 | >6 months |
| Patient L | 75 mg | Seroquel ® (quetiapine) 1200 mg | 0 | 3 weeks |
| Patient M | 400 mg | Clozapine 475 mg | Lorazepam 1 mg tid | >6 months |
| Patient N | 400 mg | Clozapine 600 mg | Lorazepam 2 mg tid | >6 months |
| Patient O | 300 mg | Clozapine 900 mg | Lorazepam 1.5 mg tid | >6 months |
| Patient P | 400 mg | Clozapine 900 mg | Clonazepam 1.25 mg tid | >6 months |

TABLE NO. 2-continued

Patient treatment plan at time of second BFCRS examination.

| Patient | Daily Dosage of Lamotrigine | Dosage of Antipsychotic | Dosage of Benzodiazepine | Length of treatment |
|---|---|---|---|---|
| Patient Q | 175 mg | Olanzapine 40 mg | Lorazepam 1 mg tid | 3 months |
| Patient R | 200 mg | Olanzapine 5 mg | Diazepam 5 mg tid | 3 months |
| Patient S | 200 mg | Clozapine 400 mg | Lorazepam 1 mg tid | 4 months |
| Patient T | 125 mg | Olanzapine 20 mg | Lorazepam 2 mg tid | 2 months |
| Patient U | 400 mg | Clozapine 900 mg | Lorazepam 1.5 mg tid | >6 months |
| Patient V | 400 mg | Clozapine 650 mg | Lorazepam 1.5 mg bid, 1 mg qhs | >6 months |
| Patient W | 400 mg | Clozapine 600 mg | Lorazepam 2 mg tid | >6 months |
| Patient X | 250 mg | Clozapine 450 mg | Lorazepam 1 mg tid | 3 months |

In secure residential settings with 39 subject beds available, there were 20 confirmed cases of catatonia. This amount of catatonia is in and of itself quite significant. However, on a percentage basis it approximates the amount of catatonia seen in the other aforementioned clinical context. Of these cases, there are 11 subjects who responded to transitioning to clozapine monotherapy with subsequent augmentation with lamotrigine. While subjects did show benefit from clozapine in some of the core components of psychotic processing, it was apparent that the addition of lamotrigine was of additional benefit in that subjects had cognitive improvements due to a reduction in the severity of catatonia. Moreover, the observed reduction in catatonic features was accompanied by "gain of function" improvements that were seen in a variety of contexts. Some specific examples of "gain of function" improvements included a subject who had been almost fully mute for several years who began speaking spontaneously. Another example was a subject with a years long history of withdrawing/menacing/agitated/aggressive behaviors and poor self-care who became remarkably more able to participate socially, less aggressive, and then began spontaneously engaging in personal hygiene tasks such as showering. Still another example of gain of function response to treatment with lamotrigine in a subject whose BFCRS score dropped from 17 to 11 in the 3 weeks after starting the combination therapy with marked improvements in impulsivity and working memory. These improvements continued in association with continued upward titration of lamotrigine.

Other common improvements due to the therapeutic interventions described herein include reductions in perseverative behaviors, stereotyped behaviors, agitation, and impulsivity. Also apparent was that some subjects became more participatory in peer-based social outings, groups, and meetings.

Additional examples from non-secure residential settings include sites where 10 out of 14 schizophrenic patients were confirmed to demonstrate catatonic features and subsequently showed marked treatment response when treated with an antipsychotic, lamotrigine, and in some cases with a benzodiazepine. As previously noted, it has been clinically evident that patients had reductions in catatonic features and thus improved cognition, improved socialization, and improved day-to-day functioning in a variety of self-care domains.

Specific examples from the non-secure residential settings include a patient who was nearly mute, perseverative, ambitendent, verbigerative, posturing and withdrawn/unresponsive/bedridden in some cases for greater than 24 hours. This subject, with an original BFCRS score of 31, had been a poor responder to clozapine and lorazepam. After augmentation with lamotrigine, the subject showed near complete cessation of any features of catatonia (follow up BFCRS score of 0). Another subject also showed a dramatic reduction in posturing, mannerisms, and impulsive screaming associated with marked gain of function improvements of spontaneous socialization, working memory, community independence, and self-care when a partially successful plan utilizing olanzapine was later augmented with lamotrigine. This patient had a BFCRS score reduced from 14 to 0 with the addition of lamotrigine.

It should be additionally noted that other cases have benefited greatly from a benzodiazepine being added to existing treatment plans that already included either clozapine or olanzapine augmented with lamotrigine (See Tables No. 1C and 1D). On the other hand, some cases showed meaningful improvement when olanzapine or clozapine replaced another antipsychotic that was being administered and augmented with lamotrigine and a benzodiazepine. Therefore, a treatment regimen that includes effective amounts of clozapine or olanzapine, lamotrigine, and a benzodiazepine, such as lorazepam, is highly effective for treating treatment resistant schizophrenics exhibiting catatonic features as determined by BFCRS scores. As well, while the combination of an antipsychotic, lamotrigine (or similar drug), and a benzodiazepine is particularly effective, the order of drug delivery may be successfully be varied, such that a patient may receive the drugs in any order, two at a time followed by the third, one followed by the remaining two, or all at once. Dosages that include one, two, or three of the drugs are contemplated herein.

Overall, these results suggest that a large percentage of schizophrenics defined as treatment resistant have a high proportion of catatonic features in addition to their psychotic symptoms. It is believed that the combination of these two dysfunctional symptom clusters creates this diagnostically challenging and difficult to treat population. Effected individuals who had previously been poor treatment responders have shown signs of improvement in their hallucinations and delusion; however, the most beneficial component of treatment response has been an increase in spontaneous, organized thoughts/behaviors in many observable domains. Behaviors such as agitation or violence become quiescent, as well. Such improvements can allow individuals who have been chronically institutionalized to step down into less restrictive community environments in a safe and sustainable manner. Thus, the care burden as well as the cost (which can be approximately 10,000 to 20,000 dollars per month) can be greatly reduced.

Moreover, these results demonstrate that administration of lamotrigine alone reduces catatonic features in subjects. A reduction in catatonic features is seen with as little as 25 mg of lamotrigine per day. Greater reduction in catatonic features in subjects was seen as the amount of lamotrigine was increased, and in some instances complete remission of catatonic features was observed. Based on these results, the administration of lamotrigine alone provides an effective treatment regimen for individuals suffering from catatonia without the need for a benzodiazepine. However, the combination of lamotrigine with other drugs (including a benzodiazepine) also provides an effective treatment regimen for individuals suffering from catatonia as well as psychotic disorders with catatonic features. Indeed, it is contemplated that individuals suffering from psychiatric disorders including, for example, Alzheimer's, dementias, and autism, and the like, who exhibit catatonic features may benefit from treatment regimens directed at countering their catatonic symptom cluster.

In other disorders such as autism or dementias (where catatonic features such as stereotypy, combativeness, impulsive wandering, screaming, verbigeration, and perseveration are potentially of great concern), use of antipsychotics and benzodiazepines may be problematic due to side effect concerns such as extra pyramidal symptoms, tardive dykinesia, weight gain, diabetes, sedation, and poor ambulation (fall risk is of specific concern in elderly populations utilizing benzodiazepines). Therefore, the treatment regimen of the present disclosure may offer such subjects a significant reduction in catatonia and therefore care burden without the need for an antipsychotic and/or a benzodiazepine.

Table No. 3 below provides predicted treatment responses in subjects exhibiting catatonic features who receive a pharmaceutical compound that reverses or negates the effects of an NMDA receptor antagonist (e.g., lamotrigine). The response is per dose over time. The treatment dosages are additive, in that, a subject receives 25 mg for 2 weeks, then the dosage is increased by 25 mg and maintained for an additional 2 weeks, and so on, until the subject reaches a maximal dosage. The dosage regimens presented below are for the purpose of illustration and additional dosage regimens are considered to be effective.

TABLE NO. 3

Predicted treatment responses to a pharmaceutical compound that reverses or negates the effects of an NMDA receptor antagonist per dosage over time.

| Dosage | Duration of treatment | Cumulative drop in BFCRS score |
|---|---|---|
| 25 mg per day | 2 weeks | 4 (±2) |
| 50 mg per day | 2 weeks | 6 (±2) |
| 75 mg per day | 2 weeks | 8 (±2) |
| 100 mg per day | 2 weeks | 10 (±2) |
| 200 mg twice per day | indefinite | maximal |

In reference to Table No. 3, it is important to note that a decrease in catatonic features will be associated with gain of function improvements such as in improved working memory, judgment, and planning. These improvements are anticipated to start with a regimen of 25 mg/day after 2 weeks. Further gain of function improvements are anticipated as the duration of treatment, but not necessarily dosage, with the compound (e.g., lamotrigine) increases.

Similarly, Table No. 4 below provides predicted treatment responses in subjects exhibiting catatonic features who receive a pharmaceutical compound that reverses or negates the effects of an NMDA receptor antagonist (e.g., lamotrigine) and an antipsychotic (LA dose). The response is per dose over time. The dosage regimens presented below are for the purpose of illustration and additional dosage regimens are considered to be effective.

TABLE NO. 4

Predicted treatment responses to LA per dosage over time.

| Dosage of Lamotrigine | Dosage of Antipsychotic* | Duration of treatment | Cumulative drop in BFCRS score |
|---|---|---|---|
| 50 mg per day | 400 mg (40 mg) | 1 month | 5 (±3) |
| 200 mg per day | 400 mg (40 mg) | 3 months | 15 (±3) |
| 400 mg per day | 400 mg (40 mg) | >6 months | maximal |

*The dosage indicated is of clozapine per day, the dosage within the parentheses is olanzapine per day.

Table No. 5 below provides predicted treatment responses in subjects exhibiting catatonic features who receive a pharmaceutical compound that reverses or negates the effects of an NMDA receptor antagonist (e.g., lamotrigine), an antipsychotic, and a benzodiazepine (LAB dose). The response is per dose over time. The dosage regimens presented below are for the purpose of illustration and additional dosage regimens are considered to be effective.

TABLE NO. 5

Predicted treatment responses to LAB per dosage over time.

| Dosage of Lamotrigine | Dosage of Antipsychotic* | Dosage of Benzodiazepine | Duration of treatment | Cumulative drop in BFCRS score |
|---|---|---|---|---|
| 200 mg per day | 400 mg (40 mg) | 3 mg per day | 3 months | 15 (±3) |
| 400 mg per day | 400 mg (40 mg) | 3 mg per day | >6 months | maximal |

*The dosage indicated is of clozapine per day, the dosage within the parentheses is olanzapine per day.

It is anticipated that significant gain of function improvements will accompany the reductions in catatonic features, as measured by BFCRS scores, due to treatment with the indicated LA and LAB dosages.

What is claimed is:

1. A method of treating a psychotic or neurological disorder comprising catatonic features in a subject in need thereof, comprising administering to the subject a therapeutically effective amount of a pharmaceutical compound comprising lamotrigine for a period of at least about 2 weeks to decrease the subject's BFCRS score by at least about 2.

2. The method of claim 1, wherein the amount of the pharmaceutical compound is at least about 25 mg per day.

3. The method of claim 1, wherein administration of at least about 50 mg per day of the pharmaceutical compound to a subject in need thereof for a period of about 4 weeks results in a decrease in the subject's BFCRS score of about 6.

4. The method of claim 1, wherein the psychotic or neurological disorder comprises catatonia, schizophrenia, Alzheimer's, dementia, autism, or combinations thereof.

5. The method of claim 1 further comprising administering a therapeutically effective amount of a benzodiazepine.

* * * * *